United States Patent
Grasruck et al.

(10) Patent No.: US 11,925,501 B2
(45) Date of Patent: Mar. 12, 2024

(54) TOPOGRAM-BASED FAT QUANTIFICATION FOR A COMPUTED TOMOGRAPHY EXAMINATION

(71) Applicant: Siemens Healthcare GmbH, Erlangen (DE)

(72) Inventors: Michael Grasruck, Eckental Forth (DE); Thomas Flohr, Uehlfeld (DE); Bernhard Schmidt, Fuerth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 491 days.

(21) Appl. No.: 16/697,363

(22) Filed: Nov. 27, 2019

(65) Prior Publication Data

US 2020/0178920 A1 Jun. 11, 2020

(30) Foreign Application Priority Data

Dec. 6, 2018 (EP) .................................... 18210794

(51) Int. Cl.
*A61B 6/00* (2006.01)
*A61B 5/00* (2006.01)
*A61B 6/03* (2006.01)

(52) U.S. Cl.
CPC ............ *A61B 6/545* (2013.01); *A61B 5/0033* (2013.01); *A61B 5/4872* (2013.01); *A61B 6/032* (2013.01); *A61B 6/5205* (2013.01)

(58) Field of Classification Search
CPC ... A61B 6/5205; A61B 5/0033; A61B 5/4872; A61B 6/032; A61B 6/545; A61B 6/488; A61B 8/085; A61B 8/5215; G06N 20/00; G06T 7/0012; G06T 2207/10081;
(Continued)

(56) References Cited

U.S. PATENT DOCUMENTS

| 8,086,012 B2 | 12/2011 | Toth et al. |
| 2003/0045792 A1 | 3/2003 | Heckel et al. |

(Continued)

FOREIGN PATENT DOCUMENTS

| CN | 106355574 A | 1/2017 |
| CN | 107205706 A | 9/2017 |

OTHER PUBLICATIONS

Makrogiannis et al., "Automated Abdominal Fat Quantification and Food Residue Removal in CT", Jan. 9-10, 2012, 2012 IEEE Workshop on Mathematical Methods in Biomedical Image Analysis, pp. 81-86 (Year: 2012).*

(Continued)

*Primary Examiner* — Patricia J Park
*Assistant Examiner* — Adil Partap S Virk
(74) *Attorney, Agent, or Firm* — Harness, Dickey & Pierce, P.L.C.

(57) ABSTRACT

In one embodiment, a method is for calculating an examination parameter for a computed tomography examination of an area of interest of a patient. The method includes receiving a topogram of the area of interest of the patient; determining fat distribution information by applying a trained machine learning algorithm onto the topogram; and calculating the examination parameter for the computed tomography examination of the area of interest of the patient based on the fat distribution information.

15 Claims, 5 Drawing Sheets

(58) Field of Classification Search
CPC ...... G06T 2207/20081; G06V 2201/03; G06V 10/25; G16H 40/63; G16H 50/20
See application file for complete search history.

(56) References Cited

U.S. PATENT DOCUMENTS

| | | | |
|---|---|---|---|
| 2006/0052690 A1* | 3/2006 | Sirohey | A61B 6/481 600/420 |
| 2010/0098310 A1* | 4/2010 | Toth | A61B 5/411 382/131 |
| 2011/0075900 A1* | 3/2011 | Masumoto | G06T 7/0012 382/128 |
| 2011/0164798 A1* | 7/2011 | Masumoto | G06T 7/12 382/131 |
| 2014/0016846 A1* | 1/2014 | Blaskovics | G06T 7/0012 382/128 |
| 2014/0270053 A1* | 9/2014 | Larson | A61B 6/545 378/4 |
| 2017/0319150 A1 | 11/2017 | Goto et al. | |
| 2018/0014745 A1 | 1/2018 | Senegas et al. | |
| 2018/0100907 A1 | 4/2018 | Soza et al. | |
| 2018/0144472 A1* | 5/2018 | Kullberg | G06T 7/11 |
| 2018/0165808 A1* | 6/2018 | Bagci | G06V 10/44 |
| 2020/0000425 A1* | 1/2020 | Ji | A61B 6/037 |
| 2020/0160982 A1* | 5/2020 | Gurson | G06N 3/08 |

OTHER PUBLICATIONS

Christner et al., "Size-specific Dose Estimates for Adult Patients at CT of the Torso", Dec. 2012, Radiology, vol. 265 No. 3, pp. 841-847 (Year: 2012).*

Hussein et al., "Context Driven Label Fusion for Segmentation of Subcutaneous and Visceral Fat in CT Volumes", Dec. 15, 2015 (Year: 2015).*

Wang et al., "A two-step convolutional neural network based computer-aided detection scheme for automatically segmenting adipose tissue volume depicting on CT images", 2017, Computer Methods and Programs in Biomedicine 144 97-104 (Year: 2017).*

Kim et al., "Optimal CT Number Range for Adipose Tissue When Determining Lean Body Mass in Whole-Body F-18 FDG PET/CT Studies", 2012, Nucl Med Mol Imaging 46:294-299 (Year: 2012).*

Peng, Wanlin et al. "A CONSORT-compliant prospective randomized controlled trial; radiation dose reducing in computed tomography using an additional lateral scout view combined with automatic tube current modulation" Medicine, vol. 96, No. 30, Jul. 1, 2017 (Jul. 1, 2017) // US ISSN: 0025-7974, DOI: 10.1097/MD. 0000000000007324.

European Search Report for European Patent Application No. 18210794 dated May 21, 2019.

* cited by examiner

IM

IM

IM

TOPOGRAM-BASED FAT QUANTIFICATION FOR A COMPUTED TOMOGRAPHY EXAMINATION

PRIORITY STATEMENT

The present application hereby claims priority under 35 U.S.C. § 119 to European patent application number EP 18210794.6 filed Dec. 6, 2018, the entire contents of which are hereby incorporated herein by reference.

FIELD

Embodiments of the invention generally relate to a method for calculating an examination parameter for a computed tomography examination; a calculating device for calculating an examination parameter for a computed tomography examination; and a computed tomography device.

BACKGROUND

For several clinical questions it is of interest to know the amount of visceral fat in the torso, ideally separated from the amount of subcutaneous fat. Beside the general wish for that information from a clinical standpoint, in particular for computed tomography (CT) imaging and radiation dose optimization, there is the wish to have this additional information available.

In case of higher amount of visceral fat, intrinsically the tissue contrast is better. Lymph nodes, malignant lesions or also other structures have a better contrast if they are embedded in a fatty environment. For example, a soft tissue structure may have a contrast of about 150 HU vs. a visceral fat environment and a contrast of 0 HU to about 50 HU (for cystic structures) vs. a soft tissue environment. As a consequence, due to the higher contrast in case of higher amounts of visceral fat, lower radiation dose or less contrast media can be used without compromising image quality and therefore diagnosis made from CT images.

SUMMARY

The amount of visceral fat and its separation from subcutaneous fat can be done from CT images that have been generated based on x-ray projection data. However, the inventors have discovered that for CT dose optimization purposes, the fat distribution information would have to be available prior to the acquisition of x-ray projection data.

At least one embodiment of the invention facilitates an improved CT dose optimization with regard to the fat distribution. The claims are related to further aspects and embodiments of the invention.

In one embodiment, the invention relates to a method for calculating an examination parameter for a computed tomography examination of an area of interest of a patient, comprising:
  receiving a topogram of the area of interest of the patient;
  determining fat distribution information by applying a trained machine learning algorithm onto the topogram, wherein the fat distribution information comprises distribution information regarding visceral fat of the patient and distribution information regarding subcutaneous fat of the patient; and
  calculating the examination parameter for the computed tomography examination of the area of interest of the patient based on the fat distribution information.

In a further embodiment, a method for calculating an examination parameter for a computed tomography examination of an area of interest of a patient is hereby disclosed, comprising:
  receiving a topogram of the area of interest of the patient;
  determining fat distribution information by applying a trained machine learning algorithm onto the topogram; and
  calculating the examination parameter for the computed tomography examination of the area of interest of the patient based on the fat distribution information.

In one further embodiment, the invention relates to a calculating device for calculating an examination parameter for a computed tomography examination of an area of interest of a patient, comprising:
  a topogram receiver for receiving topogram of the area of interest of the patient;
  a fat distribution information determiner for determining fat distribution information by applying a trained machine learning algorithm onto the topogram, wherein the fat distribution information comprises distribution information regarding visceral fat of the patient and distribution information regarding subcutaneous fat of the patient; and
  an examination parameter calculator for calculating the examination parameter for the computed tomography examination of the area of interest of the patient based on the fat distribution information.

In a further embodiment, a calculating device for calculating an examination parameter for a computed tomography examination of an area of interest of a patient is hereby disclosed, comprising:
  a topogram receiver for receiving topogram of the area of interest of the patient;
  a fat distribution information determiner for determining fat distribution information by applying a trained machine learning algorithm onto the topogram; and
  an examination parameter calculator for calculating the examination parameter for the computed tomography examination of the area of interest of the patient based on the fat distribution information.

In one further embodiment, the invention relates to a computed tomography device, comprising:
  a calculating device according to one or more of the disclosed embodiments for calculating an examination parameter for a computed tomography examination of an area of interest of a patient; and
  an x-ray source for irradiating the area of interest of the patient with x-rays based on the examination parameter.

In one further embodiment, the invention relates to a computer program product comprising program elements which induce a calculating device to carry out the steps of the method according to one or more of the disclosed embodiments, when the program elements are loaded into a memory of the calculating device.

In one further embodiment, the invention relates to a computer-readable medium on which program elements are stored that can be read and executed by a calculating device, in order to perform the steps of the method according to one or more of the disclosed embodiments, when the program elements are executed by the calculating device.

In one further embodiment, the invention relates to a method for calculating an examination parameter for a computed tomography examination of an area of interest of a patient, comprising:

receiving a topogram of the area of interest of the patient;

determining fat distribution information by applying a trained machine learning algorithm to the topogram, wherein the fat distribution information includes distribution information regarding visceral fat of the patient and distribution information regarding subcutaneous fat of the patient; and calculating the examination parameter for the computed tomography examination of the area of interest of the patient based on the fat distribution information determined.

In one further embodiment, the invention relates to a calculation device for calculating an examination parameter for a computed tomography examination of an area of interest of a patient, comprising:

a topogram receiver to receive a topogram of the area of interest of the patient;

a fat distribution information determiner to determine fat distribution information by applying a trained machine learning algorithm to the topogram, the fat distribution information including distribution information regarding visceral fat of the patient and distribution information regarding subcutaneous fat of the patient; and an examination parameter calculator to calculate the examination parameter for the computed tomography examination of the area of interest of the patient based on the fat distribution information determined.

BRIEF DESCRIPTION OF THE DRAWINGS

The invention will be illustrated below with reference to the accompanying figures using example embodiments. The illustration in the figures is schematic and highly simplified and not necessarily to scale.

DETAILED DESCRIPTION OF THE EXAMPLE EMBODIMENTS

Figure 1:
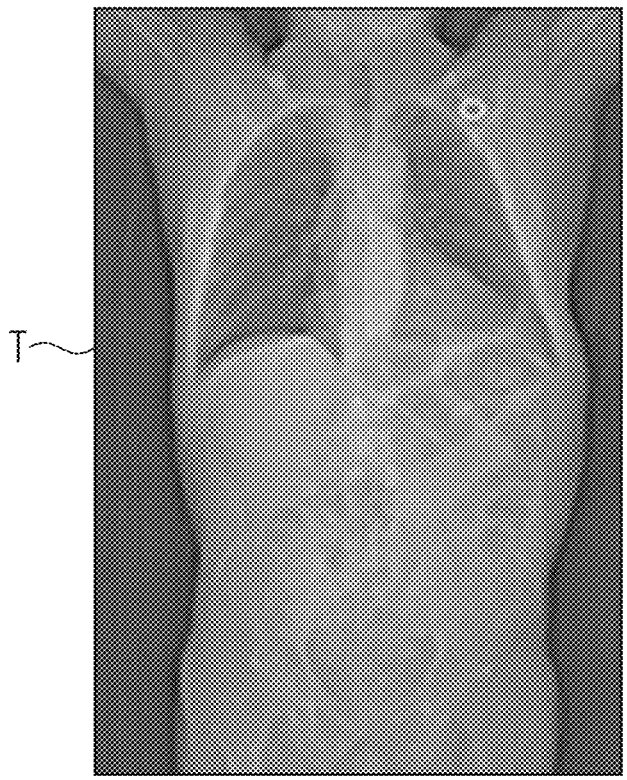
FIG. 1 shows a topogram of a normal patient.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In one embodiment, the invention relates to a method for calculating an examination parameter for a computed tomography examination of an area of interest of a patient, comprising:
    receiving a topogram of the area of interest of the patient;
    determining fat distribution information by applying a trained machine learning algorithm onto the topogram, wherein the fat distribution information comprises distribution information regarding visceral fat of the patient and distribution information regarding subcutaneous fat of the patient; and
    calculating the examination parameter for the computed tomography examination of the area of interest of the patient based on the fat distribution information.

In a further embodiment, a method for calculating an examination parameter for a computed tomography examination of an area of interest of a patient is hereby disclosed, comprising:
- receiving a topogram of the area of interest of the patient;
- determining fat distribution information by applying a trained machine learning algorithm onto the topogram; and
- calculating the examination parameter for the computed tomography examination of the area of interest of the patient based on the fat distribution information.

The topogram may comprise x-ray attenuation data of the area of interest of the patient. The topogram may be acquired by the computed tomography device without rotating the x-ray source around the patient.

The distribution information regarding visceral fat may comprise a distribution of visceral fat along a patient length axis. The distribution information regarding subcutaneous fat may comprise a distribution of subcutaneous fat along the patient length axis. According to one embodiment, the trained machine learning algorithm is configured to separate, based on the topogram, fat from soft tissue. According to one embodiment, the trained machine learning algorithm is configured to separate, based on the topogram, different fat components from each other, for example visceral fat from subcutaneous fat.

In another embodiment the examination parameter is an x-ray exposure parameter and/or the examination parameter is calculated by applying an automatic exposure control algorithm, for example, with an automatic exposure control calculator, onto the fat distribution information.

The examination parameter may be, for example, an x-ray tube current. The x-ray tube current may be specified, for example, in milliamps. To achieve a comparable image quality, a lower dose, and therefore a lower x-ray tube current, is required for an area of interest of a patient comprising a relatively high percentage of visceral fat than for an area of interest of a patient comprising a relatively high percentage of subcutaneous fat.

In another embodiment the examination parameter is a contrast medium administration parameter. The contrast medium administration parameter may be, for example, an amount or a concentration of contrast medium.

According to one embodiment, the trained machine learning algorithm is configured to determine an examination parameter set, the examination parameter set comprising the examination parameter and at least one further examination parameter. According to one embodiment, the trained machine learning algorithm is configured to determine a series of examination parameters and/or a series of examination parameter sets. The series may be a time series and/or relate each of the examination parameters of the series to a rotation angle of the x-ray source with respect to the patient.

Therefore, the fat distribution information can be utilized for optimizing dose values and/or parametrizations of automatic exposure control techniques prior to the computed tomography examination.

In another embodiment, the method further comprises:
- receiving a plurality of training samples, each training sample of the plurality of training samples comprising a topogram sample and a corresponding fat distribution information sample; and
- training the machine learning algorithm based on the plurality of training samples.

Each training sample of the plurality of training samples may comprise a topogram sample of a patient to whom that training sample relates and a corresponding fat distribution information sample of the patient to whom that training sample relates. For each patient of a plurality of patients, the plurality of training samples may comprise a training sample that is related to that patient.

In another embodiment, each training sample of the plurality of training samples further comprises a computed tomography image sample, in particular of the patient to whom that training sample relates, corresponding to the topogram sample.

Based on available topograms and corresponding visceral and subcutaneous fat distributions, obtained, for example, from computed tomography images, the machine learning algorithm can be trained and thereby configured to determine the fat distribution information based on the topogram.

A corresponding fat distribution information samples may comprise corresponding distribution information regarding visceral fat of the patient and/or corresponding distribution information regarding subcutaneous fat of the patient.

The machine learning algorithm can learn, for example, the relationships between structures and attenuation values, the regional distributions/appearances of fat, and, in particular, the subcutaneous and visceral fat distributions in topograms and/or in computed tomography images. After successful training, information about the subcutaneous and visceral fat distributions is available based on the topogram only, and therefor prior to the computed tomography examination.

In another embodiment, each training sample of the plurality of training samples further comprises a corresponding fat quantification sample indicative of an overall fat content of a patient to whom that training sample relates. In another embodiment the machine learning algorithm is configured for determining a fat quantification indicative of an overall fat content of the patient.

A fat quantification indicative of an overall fat content of the patient may be, for example a body mass index (BMI) of the patient or a body fat percentage of the patient. The machine learning algorithm may be configured for determining a visceral fat quantification indicative of an overall visceral fat content of the patient and/or for determining a subcutaneous fat quantification indicative of an overall subcutaneous fat content of the patient. Therefore, an overall fat content of the patient may be estimated based on a topogram that covers only a relatively small portion of the patient. The fat quantification may be automatically recorded in the clinical report that is generated based on the tomogram and/or the medical image.

In another embodiment, the method further comprises:
- irradiating the area of interest of the patient with x-rays based on the examination parameter.

The irradiating the area of interest of the patient with x-rays based on the examination parameter may comprise generating x-rays, with an x-ray tube, based on the examination parameter. The irradiating the area of interest of the patient with x-rays based on the examination parameter may comprise providing contrast medium in the area of interest of the patient based on the contrast medium administration parameter.

In another embodiment, the method further comprises:
- acquiring projection data of the area of interest of the patient based on the x-rays, in particular, while rotating the x-ray source and the x-ray detector around the patient,
- generating a medical image based on the projection data, and
- providing the medical image.

In one further embodiment, the invention relates to a calculating device for calculating an examination parameter for a computed tomography examination of an area of interest of a patient, comprising:
- a topogram receiver for receiving topogram of the area of interest of the patient;
- a fat distribution information determiner for determining fat distribution information by applying a trained machine learning algorithm onto the topogram, wherein the fat distribution information comprises distribution information regarding visceral fat of the patient and distribution information regarding subcutaneous fat of the patient; and
- an examination parameter calculator for calculating the examination parameter for the computed tomography examination of the area of interest of the patient based on the fat distribution information.

In a further embodiment, a calculating device for calculating an examination parameter for a computed tomography examination of an area of interest of a patient is hereby disclosed, comprising:
- a topogram receiver for receiving topogram of the area of interest of the patient;
- a fat distribution information determiner for determining fat distribution information by applying a trained machine learning algorithm onto the topogram; and
- an examination parameter calculator for calculating the examination parameter for the computed tomography examination of the area of interest of the patient based on the fat distribution information.

In another embodiment, the calculating device further comprises:
- a training sample receiver for receiving a plurality of training samples, each training sample of the plurality of training samples comprising a topogram sample and a corresponding fat distribution information sample,
- an algorithm trainer for training the machine learning algorithm based on the plurality of training samples.

In another embodiment, the calculating device is configured to implement the method according to one or more of the disclosed embodiments.

In one further embodiment, the invention relates to a computed tomography device, comprising:
- a calculating device according to one or more of the disclosed embodiments for calculating an examination parameter for a computed tomography examination of an area of interest of a patient; and
- an x-ray source for irradiating the area of interest of the patient with x-rays based on the examination parameter.

In one further embodiment, the invention relates to a computer program product comprising program elements which induce a calculating device to carry out the steps of the method according to one or more of the disclosed embodiments, when the program elements are loaded into a memory of the calculating device.

In one further embodiment, the invention relates to a computer-readable medium on which program elements are stored that can be read and executed by a calculating device, in order to perform the steps of the method according to one or more of the disclosed embodiments, when the program elements are executed by the calculating device.

Any of the algorithms mentioned herein may be based on one or more of the following architectures: convolutional neural networks, deep belief networks, deep residual learning, deep reinforcement learning, recurrent neural networks, Siamese networks, generative adversarial networks or autoencoders. In particular, the trained machine learning algorithm for determining the fat distribution information may be embodied as a deep learning algorithm and/or as a convolutional neural network.

Any of the components mentioned herein or any interface between the components may be embodied in form of hardware and/or software. In particular, an interface may be embodied in form of at least one of a PCI-Bus, a USB or a Firewire. In particular, a component can comprise hardware elements and/or software elements, for example a microprocessor, a field programmable gate array (an acronym is "FPGA") or an application specific integrated circuit (an acronym is "ASIC").

The calculating device can, for example, comprise and/or be a part of at least one of a cloud-computing system, a distributed computing system, a computer network, a computer, a tablet computer, a smartphone or the like. The calculating device can comprise hardware and/or software. The hardware may be, for example, a processor system, a memory system and combinations thereof. The hardware may be configurable by the software and/or be operable by the software. Calculations for performing steps of a method and/or for training an algorithm may be carried out in a processor.

Data, in particular, the plurality of training samples, may be received, for example, by receiving a signal that carries the data and/or by reading the data from a computer-readable medium. Data, in particular, the medical image, may be provided, for example, by transmitting a signal that carries the data and/or by writing the data into a computer-readable medium and/or by displaying the data on a display.

The computer program product may be, for example, a computer program or comprise another element apart from the computer program. This other element may be hardware, for example a memory device, on which the computer program is stored, a hardware key for using the computer program and the like, and/or software, for example, documentation or a software key for using the computer program. A computer-readable medium may be embodied as non-permanent main memory (e.g. random access memory) or as permanent mass storage (e.g. hard disk, USB stick, SD card, solid state disk).

A computer-readable medium on which program elements are stored that can be read and executed by an imaging data processing unit in order to perform the steps of the method according to one or more of the disclosed embodiments, when the program elements are executed by the imaging data processing unit. According to a further embodiment, the method is a computer-implemented method.

Wherever not already described explicitly, individual embodiments, or their individual aspects and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention Reference is made to the fact that the described methods and the described system are merely preferred example embodiments of the invention and that the invention can be varied by a person skilled in the art, without departing from the scope of the invention as it is specified by the claims.

Figure 2:
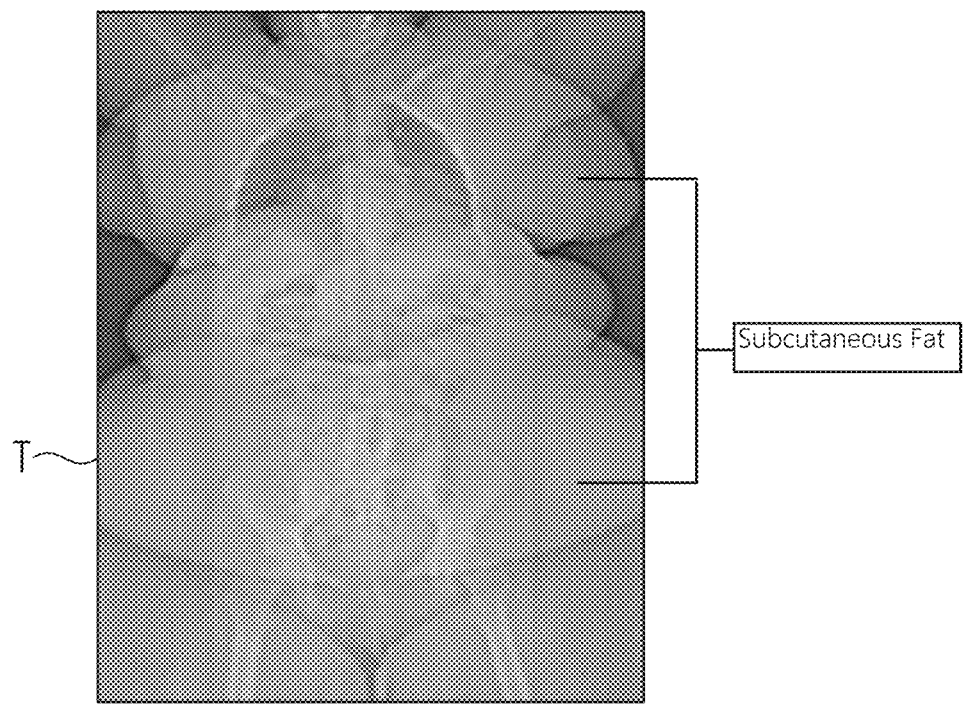
FIG. 2 shows a topogram of an obese patient with high amounts of subcutaneous fat.
Figure 3:
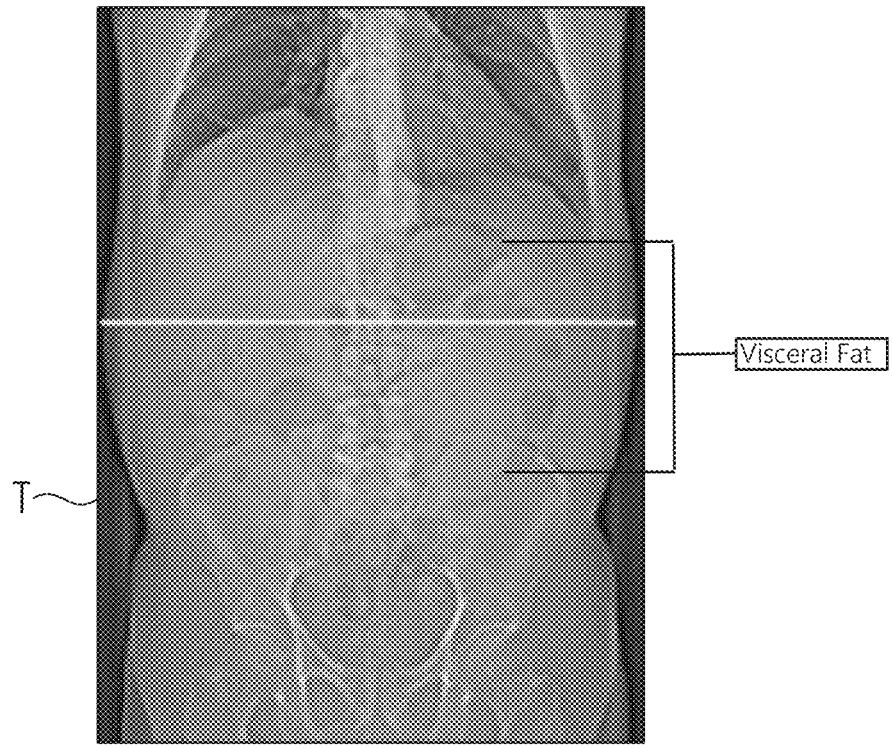
FIG. 3 shows a topogram of an obese patient with high amounts of visceral fat.

FIG. 1 shows a topogram T of a normal patient. FIG. 2 shows a topogram T of an obese patient with high amounts of subcutaneous fat. Large, fatty subcutaneous structures are clearly visible—despite the overlay with other structures— in the peripheral regions of the body (left and right side of the topogram). FIG. 3 shows a topogram of an obese patient with high amounts of visceral fat. Visceral fat is dominating more the inner portion of the topogram.

As shown in FIGS. 1-3, topograms from different patients show—to some extent—differences in the amount of overall fat and its regional distributions for the different positions along the patient length axis and between patients. Due to those differences the different amounts of fat as well as their contributions can be derived from topogram data.

Figure 4:
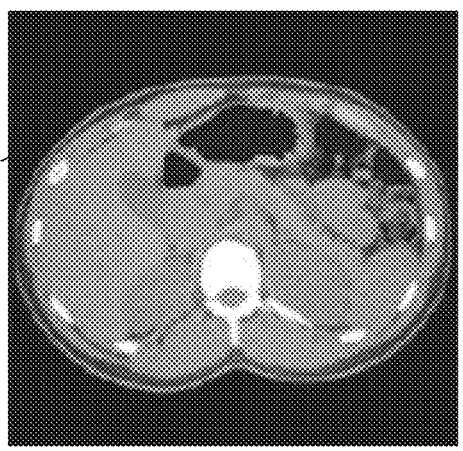
FIG. 4 shows a computed tomography image corresponding to the topogram shown in FIG. 1.
Figure 5:
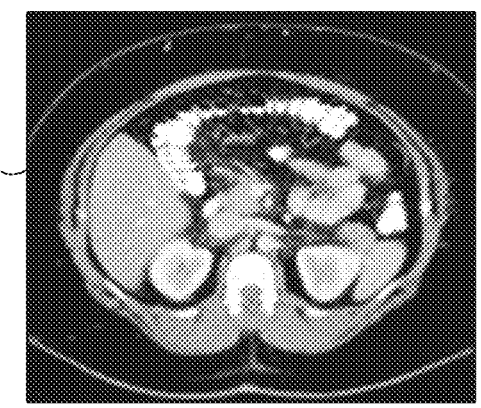
FIG. 5 shows a computed tomography image corresponding to the topogram shown in FIG. 2.
Figure 6:
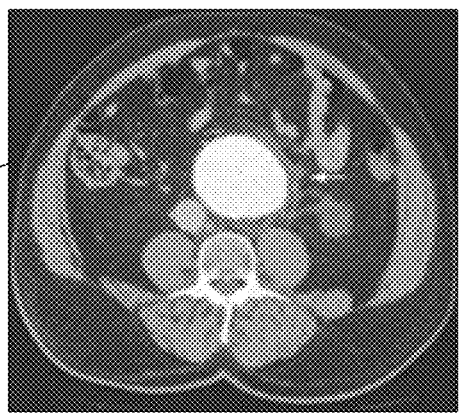
FIG. 6 shows a computed tomography image corresponding to the topogram shown in FIG. 3.

FIG. 4 shows a computed tomography image corresponding to the topogram shown in FIG. 1. FIG. 5 shows a computed tomography image corresponding to the topogram shown in FIG. 2. FIG. 6 shows a computed tomography image corresponding to the topogram shown in FIG. 3.

Figure 7:
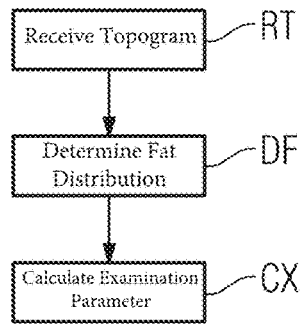
FIG. 7 shows a diagram illustrating a method for calculating an examination parameter for a computed tomography examination.

FIG. 7 shows a diagram illustrating a method for calculating an examination parameter for a computed tomography examination of an area of interest A of a patient 13, comprising:
- receiving RT a topogram T of the area of interest A of the patient 13,
- determining DF fat distribution information by applying a trained machine learning algorithm onto the topogram T, wherein the fat distribution information comprises distribution information regarding visceral fat of the patient 13 and distribution information regarding subcutaneous fat of the patient 13,
- calculating CX the examination parameter for the computed tomography examination of the area of interest A of the patient 13 based on the fat distribution information.

Figure 8:
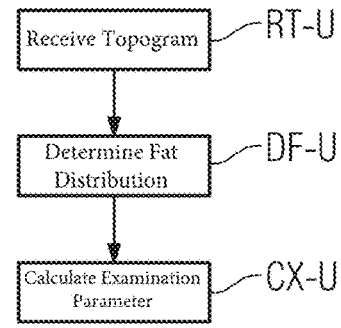
FIG. 8 shows a calculating device for calculating an examination parameter.

FIG. 8 shows a calculating device 35 for calculating an examination parameter for a computed tomography examination of an area of interest A of a patient 13, comprising:
- a topogram receiver RT-U for receiving RT topogram T of the area of interest A of the patient 13,
- a fat distribution information determiner DF-U for determining DF fat distribution information by applying a trained machine learning algorithm onto the topogram T, wherein the fat distribution information comprises distribution information regarding visceral fat of the patient 13 and distribution information regarding subcutaneous fat of the patient 13,
- an examination parameter calculator CX-U for calculating CX the examination parameter for the computed tomography examination of the area of interest A of the patient 13 based on the fat distribution information.

Figure 9:
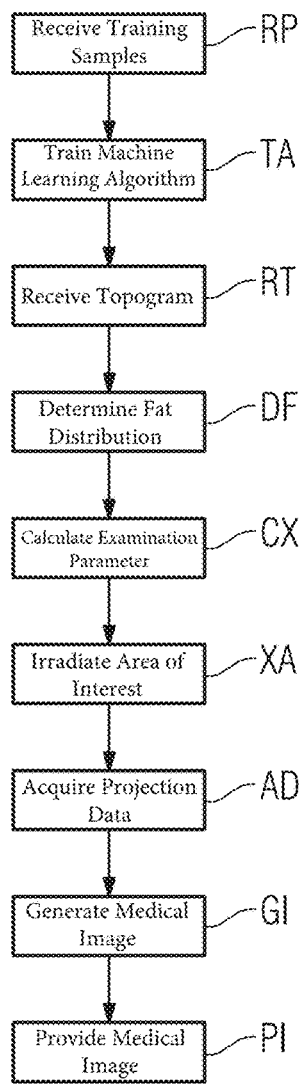
FIG. 9 shows a diagram illustrating another example embodiment of a method for calculating an examination parameter.

FIG. 9 shows a diagram illustrating a method for calculating an examination parameter for a computed tomography examination of an area of interest A of a patient 13, further comprising:
- receiving RP a plurality of training samples, each training sample of the plurality of training samples comprising a topogram sample and a corresponding fat distribution information sample,
- training TA the machine learning algorithm based on the plurality of training samples,
- irradiating XA the area of interest A of the patient 13 with x-rays 27 based on the examination parameter,
- acquiring AD projection data of the area of interest A of the patient 13 based on the x-rays,
- generating GI a medical image IM based on the projection data, and
- providing PI the medical image IM.

Figure 10:
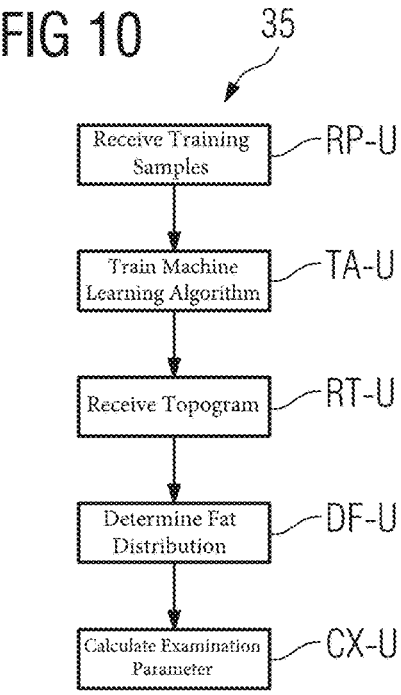
FIG. 10 shows another example embodiment of a calculating device for calculating an examination parameter.

FIG. 10 shows a calculating device 35 for calculating an examination parameter for a computed tomography examination of an area of interest A of a patient 13, further comprising:
- a training sample receiver RP-U for receiving RP a plurality of training samples, each training sample of the plurality of training samples comprising a topogram sample and a corresponding fat distribution information sample,
- an algorithm trainer TA-U for training TA the machine learning algorithm based on the plurality of training samples.

Figure 11:
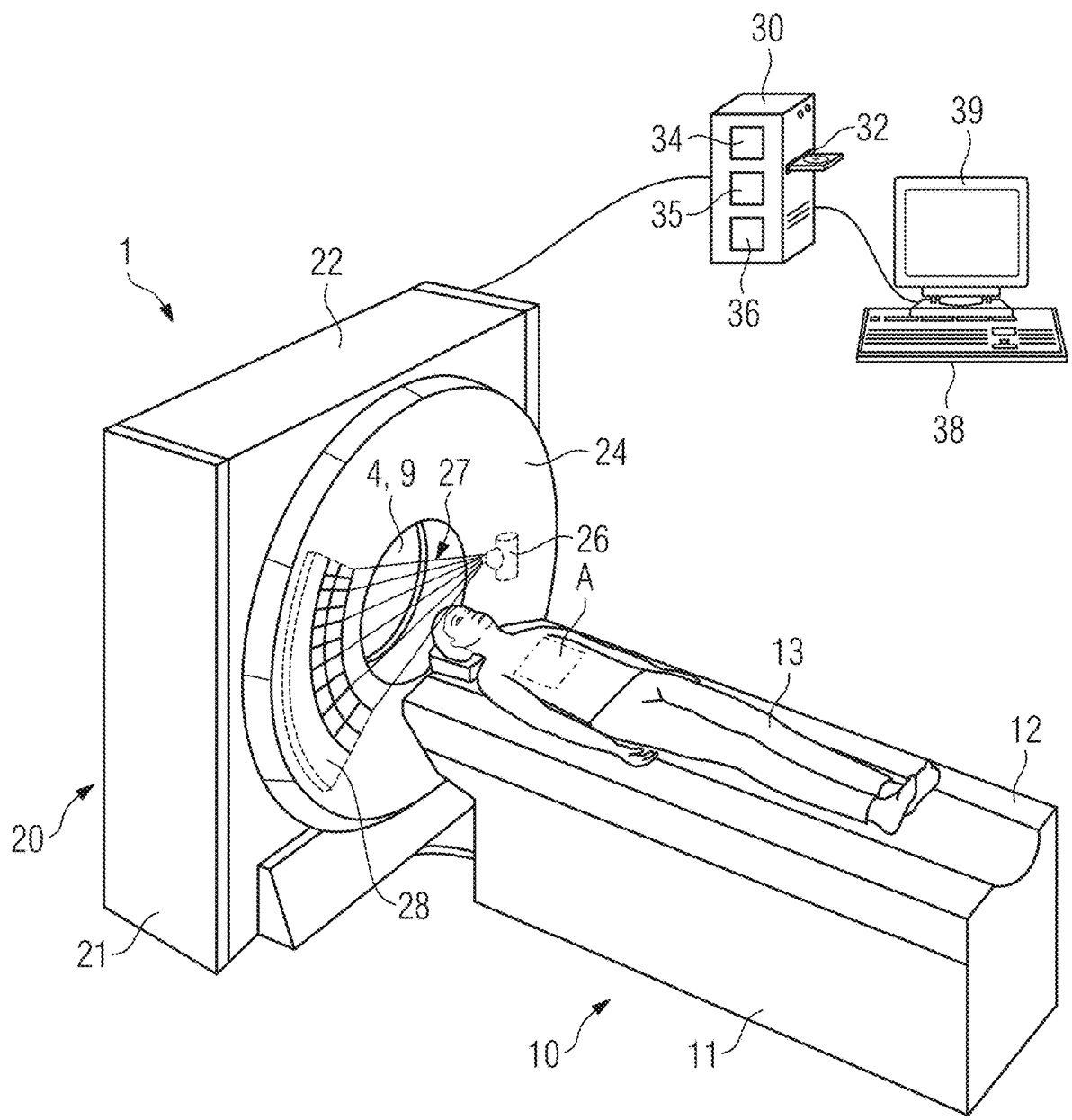
FIG. 11 shows a computed tomography device.

FIG. 11 shows a computed tomography device 1, comprising:
- a calculating device 35 according for calculating an examination parameter for a computed tomography examination of an area of interest A of a patient 13,
- an x-ray source 26 for irradiating the area of interest A of the patient 13 with x-rays 27 based on the examination parameter.

The computed tomography device 1 further comprises a gantry 20, comprising a support frame 21, a tilting frame 22, and a rotating frame 24, an x-ray source 26, an x-ray detector 28, and a patient handling system 10, comprising a base 11 and a patient transfer board 12. The patient handling system 10 is configured for placing the patient 13, by a translation movement of the transfer board 12 with respect to the base 11, in the tunnel-shaped opening 9 of the gantry 20. Thereby the area of interest A of the patient 13 can be placed in the acquisition portion 4 of the computed tomography device 1 for interaction with the x-rays 27 emitted from the x-ray source 26. The x-ray source 26 and the x-ray detector 28 are mounted on the rotating frame 24 for rotation around the acquisition portion 4 located within the tunnel-shaped opening 9.

The computed tomography device 1 further comprises a control unit 30, the control unit 30 comprising the computer-readable medium 32, the image reconstruction unit 34 for reconstructing a medical image IM based on the projection data, the calculating device 35 and the processor 36, an input unit 38 (e.g. a keyboard and/or a mouse) and a display 39 for displaying topograms T, medical images IM and/or examination parameters.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for calculating at least one examination parameter for a computed tomography examination of an area of interest of a patient, the method comprising:
   receiving a topogram of the area of interest of the patient;
   determining a fat distribution of the patient by applying a trained machine learning algorithm to the topogram, the fat distribution including a distribution of visceral fat of the patient and a distribution of subcutaneous fat of the patient, the distribution of visceral fat of the patient being a distribution of visceral fat of the patient along a patient length axis and the distribution of subcutaneous fat of the patient being a distribution of subcutaneous fat along the patient length axis; and
   calculating the at least one examination parameter for the computed tomography examination of the area of interest of the patient based on the fat distribution, wherein the calculated at least one examination parameter includes an x-ray tube current that is dependent on a percentage of visceral fat and a percentage of subcutaneous fat within the area of interest; and
   irradiating the area of interest of the patient with x-rays from an x-ray source based on the at least one examination parameter.

2. The method of claim 1, wherein at least one of
   the at least one examination parameter further includes an x-ray exposure parameter and
   the x-ray exposure parameter is calculated by applying an automatic exposure control algorithm to the fat distribution.

3. The method of claim 2, wherein the at least one examination parameter further includes a contrast medium administration parameter.

4. The method of claim 2, further comprising:
   receiving a plurality of training samples, each training sample of the plurality of training samples including a topogram sample and a corresponding fat distribution sample,
   training a machine learning algorithm based on the plurality of training samples, wherein the machine learning algorithm is the trained machine learning algorithm upon being trained.

5. The method of claim 4, wherein each training sample of the plurality of training samples further includes a computed tomography image sample corresponding to the topogram sample, the computed tomography image sample being different from the topogram sample.

6. The method of claim 1, wherein the at least one examination parameter further includes a contrast medium administration parameter.

7. The method of claim 1, further comprising:
   receiving a plurality of training samples, each training sample of the plurality of training samples including a topogram sample and a corresponding fat distribution sample, and
   training a machine learning algorithm based on the plurality of training samples, wherein the machine learning algorithm is the trained machine learning algorithm upon being trained.

8. The method of claim 7, wherein each training sample of the plurality of training samples further includes a computed tomography image sample corresponding to the topogram sample, the computed tomography image sample being different from the topogram sample.

9. The method of claim 7, wherein at least one of
   each training sample of the plurality of training samples further includes a corresponding fat quantification sample, the corresponding fat quantification sample indicating an overall fat content of each training sample, and
   wherein the trained machine learning algorithm is configured for determining a fat quantification, the fat quantification indicating an overall fat content of each training sample.

10. The method of claim 1, further comprising:
    acquiring projection data of the area of interest of the patient based on the x-rays;
    generating a medical image based on the projection data; and
    providing the medical image.

11. A computed tomography device for calculating at least one examination parameter for a computed tomography examination of an area of interest of a patient, the device comprising:
    one or more processors; and
    a memory storing computer-executable instructions that, when executed by the one or more processors, causes the computed tomography device to perform the method of claim 1.

12. A non-transitory computer-readable medium storing executable instructions that, when executed by a processor, causes the processor to perform the method of claim 1.

13. A computed tomography device for calculating at least one examination parameter for a computed tomography examination of an area of interest of a patient, the computed tomography device comprising:
    one or more processors; and
    a memory storing computer-executable instructions, when executed by the one or more processors, causes the computed tomography device to
    receive a topogram of the area of interest of the patient;
    determine a fat distribution of the patient by applying a trained machine learning algorithm to the topogram, the fat distribution including a distribution of visceral fat of the patient and a distribution of subcutaneous fat of the patient, the distribution of visceral fat of the patient being a distribution of visceral fat of the patient along a patient length axis and the distribution of subcutaneous fat of the patient being a distribution of subcutaneous fat along the patient length axis;
    calculate the at least one examination parameter for the computed tomography examination based on the fat distribution, wherein the calculated at least one examination parameter includes an x-ray tube current that is dependent on a percentage of visceral fat and a percentage of subcutaneous fat within the area of interest; and
    irradiate the area of interest of the patient with x-rays from an x-ray source of the computed tomography device based on the examination parameter.

14. The computed tomography device of claim 13, wherein, the memory storing computer-executable instructions, when executed by the one or more processors, further causes the computed tomography device to
- receive a plurality of training samples, each training sample of the plurality of training samples including a topogram sample and a corresponding fat distribution sample; and
- train a machine learning algorithm based on the plurality of training samples, wherein the machine learning algorithm is the trained machine learning algorithm upon being trained.

15. The computed tomography device of claim 13, wherein the at least one examination parameter further includes a contrast medium administration parameter.

* * * * *